(12) United States Patent
Rossi et al.

(10) Patent No.: US 8,778,397 B2
(45) Date of Patent: Jul. 15, 2014

(54) STABILIZED TOLTERODINE TARTRATE FORMULATIONS

(71) Applicant: Mylan Inc., Morgantown, WV (US)

(72) Inventors: David T. Rossi, Morgantown, WV (US); Boyong Li, Morgantown, WV (US); James Paul McCall, Grafton, WV (US)

(73) Assignee: Mylan, Inc., Morgantown, WV (US)

( * ) Notice: Subject to any disclaimer, the term of this patent is extended or adjusted under 35 U.S.C. 154(b) by 0 days.

(21) Appl. No.: 13/915,367

(22) Filed: Jun. 11, 2013

(65) Prior Publication Data

US 2013/0296439 A1    Nov. 7, 2013

Related U.S. Application Data

(62) Division of application No. 11/878,037, filed on Jul. 20, 2007, now Pat. No. 8,486,452.

(51) Int. Cl.
| | | |
|---|---|---|
| A61K 31/135 | (2006.01) | |
| A61K 9/20 | (2006.01) | |
| A61K 9/24 | (2006.01) | |
| A61P 43/00 | (2006.01) | |

(52) U.S. Cl.
USPC ............................. 424/471; 424/464; 514/648

(58) Field of Classification Search
None
See application file for complete search history.

(56) References Cited

U.S. PATENT DOCUMENTS

| | | | |
|---|---|---|---|
| 3,256,153 A | 6/1966 | Heimlich | |
| 3,696,189 A | 10/1972 | Snyder | |
| 4,994,279 A | 2/1991 | Aoki et al. | |
| 5,093,200 A | 3/1992 | Watanabe et al. | |
| 5,358,970 A | 10/1994 | Ruff | |
| 5,389,380 A | 2/1995 | Noda et al. | |
| 5,411,745 A | 5/1995 | Oshlack et al. | |
| 5,472,710 A | 12/1995 | Klokkers-Bethke et al. | |
| 5,629,017 A | 5/1997 | Pozzi et al. | |
| 5,683,722 A | 11/1997 | Derrieu et al. | |
| 5,700,484 A | 12/1997 | Chauffard et al. | |
| 5,891,475 A | 4/1999 | Perrin et al. | |
| 5,922,914 A | 7/1999 | Gage et al. | |
| 6,391,342 B1 | 5/2002 | Henriksen et al. | |
| 6,541,025 B1 | 4/2003 | Kershman et al. | |
| 6,630,162 B1 | 10/2003 | Nilvebrant et al. | |
| 6,911,217 B1 | 6/2005 | Gren et al. | |
| 6,939,560 B2 | 9/2005 | Shen et al. | |
| 6,951,655 B2 | 10/2005 | Cho et al. | |
| 7,005,449 B2 | 2/2006 | Hawley et al. | |
| 2003/0185882 A1 | 10/2003 | Vergez et al. | |
| 2004/0043073 A1 | 3/2004 | Chen et al. | |
| 2005/0042291 A1 | 2/2005 | Hawley et al. | |
| 2006/0177510 A1 | 8/2006 | Vergez et al. | |
| 2007/0203209 A1 | 8/2007 | Bartolini et al. | |

FOREIGN PATENT DOCUMENTS

| | | |
|---|---|---|
| EP | 1731142 | 12/2006 |
| JP | 2003517446 | 5/2003 |
| WO | 92/01446 | 2/1992 |
| WO | 0012069 | 3/2000 |
| WO | 2006102965 | 10/2006 |
| WO | 2006132440 | 12/2006 |

OTHER PUBLICATIONS

"Extended European Search Report for EP 07863132.2 dtd Nov. 29, 2012".
"International Search Report for PCT/US2007/025970 dated May 19, 2008".
Krishna, et al., "A Validated Stability-Indicating HPLC Method for the Determination of Related Substances and Assay of Tolterodine Tartrate", Rasyan J. Chem. 2(1) (2009), 144-150.
Saxena, et al., "Stability-indicating HPLC determination of tolterodine tartrate in pharmaceutical dosage form", Indian Journal of Chemical Technology, 13 (2006),, 242-246.
Varma, et al., "Rapid and selective UV spectrophotometric and RP-HPLC methods for dissolution studies of oxybutynin immediate-release and controlled-release formulations", Journal of Pharmaceutical and Biomedical Analysis 36 (2004), 669-674.

*Primary Examiner* — Robert A Wax
*Assistant Examiner* — Randeep Singh
(74) *Attorney, Agent, or Firm* — Kramer Amado, P.C.

(57) ABSTRACT

A method of making a pharmaceutical composition containing tolterodine L-tartrate stabilized against degradation with an acid. Acid-stabilized tolterodine L-tartrate may be used as an active ingredient in various types of immediate release and controlled release dosage forms, including tablets, capsules, and beads.

20 Claims, 5 Drawing Sheets

STABILIZED TOLTERODINE TARTRATE FORMULATIONS

CROSS-REFERENCE TO RELATED APPLICATIONS

The application is a divisional of parent U.S. application Ser. No. 11/878,037, filed on Jul. 20, 2007. The entire disclosure of the prior application is hereby incorporated by reference herein in its entirety.

BACKGROUND

The subject matter disclosed herein relates to stabilized tolterodine tartrate formulations. The subject matter further relates generally to pharmaceutical dosage forms comprising stabilized tolterodine tartrate. The subject matter additionally relates to formulations containing immediate and/or controlled release beads, and to methods of preparing said beads.

Tolterodine tartrate is a known muscarinic receptor antagonist that is used to treat urinary incontinence. Tolterodine acts on M2 and M3 subtypes of muscarinic receptors whereas most antimuscarinic treatments for overactive bladder only act on M3 receptors making them more selective. Tolterodine, although it acts on two types of receptors, has fewer side effects than other antimuscarinics, such as oxybutynin (which is selective for M3 receptors only) as tolterodine targets the bladder more than other areas of the body. This means that less drug needs to be given daily (due to efficient targeting of the bladder) and so there are fewer side effects. Common side effects of tolterodine tartrate include hyposalivation, constipation, and decreased gastric motility.

Tolterodine is highly water soluble, having solubility in water of 12 g/1000 mL. Dosage forms containing tolerodine, including both immediate release and controlled release dosage forms, suffer from the degradation of tolterodine. In particular, degradation of the tolterodine active agent may be evidenced as measurable levels of tolterodine impurities which arise in pharmaceutical dosage forms stored under normal conditions of heat and humidity. Such degradation may lead to reduction of active agent, decreased potency of the tolterodine dosage forms and unacceptably high levels of impurities resulting from the chemical degradation of tolterodine. In view of the degradation of tolterodine active agent in pharmaceutical dosage forms, there is a need for a pharmaceutical formulation and a method of preparing such formulation wherein the tolterodine active agent is protected from degradation.

SUMMARY

Various embodiments disclosed herein include solid oral dosage forms comprising an effective amount of a stabilized tolterodine L-tartrate and pharmaceutically acceptable excipients. The tolterodine L-tartrate is stabilized with a pharmaceutically acceptable pH-modifying acid.

Various embodiments disclosed herein include compositions comprising tolterodine L-tartrate, and a pharmaceutically acceptable non-polymeric pH-modifying acid having a $pK_a$ of less than 5.0. The acid is present in an amount effective for stabilizing tolterodine L-tartrate.

Various exemplary embodiments disclosed herein include methods of making a drug-containing bead. These methods include a step of combining tolterodine-L-tartrate with a stabilizing amount of a pharmaceutically acceptable pH-modifying acid to obtain an acid-stabilized tolterodine-L-tartrate. A seal layer is deposited on an inert core, where the seal layer is formed from a non-polymeric hydrophobic material; and a layer containing the acid-stabilized tolterodine-L-tartrate is then deposited on the seal layer.

Various embodiments disclosed herein include methods of making pharmaceutical compositions. These methods include a step of combining tolterodine-L-tartrate with a stabilizing amount of a pharmaceutically acceptable pH-modifying acid to obtain an acid-stabilized tolterodine-L-tartrate. The acid-stabilized tolterodine-L-tartrate is then combined with excipients.

According to certain embodiments disclosed herein, a tablet is prepared by combining tolterodine-L-tartrate with a stabilizing amount of a pharmaceutically acceptable pH-modifying acid, and then combining the resulting tolterodine-L-tartrate mixture with excipients to produce an acid-stabilized mixture. According to certain embodiments, the acid-stabilized mixture is compressed to form a tablet. According to some embodiments, the acid-stabilized mixture is filled into a capsule shell to produce a capsule.

In some embodiments, the acid-stabilized mixture is used to produce a drug-containing bead by depositing a seal layer of a non-polymeric hydrophobic material on an inert core; and depositing a layer containing the acid-stabilized mixture on the seal layer.

BRIEF DESCRIPTION OF THE DRAWINGS

In order to better understand various exemplary embodiments, reference is made to the accompanying drawings.

DETAILED DESCRIPTION OF VARIOUS EXEMPLARY EMBODIMENTS

Figure 1:
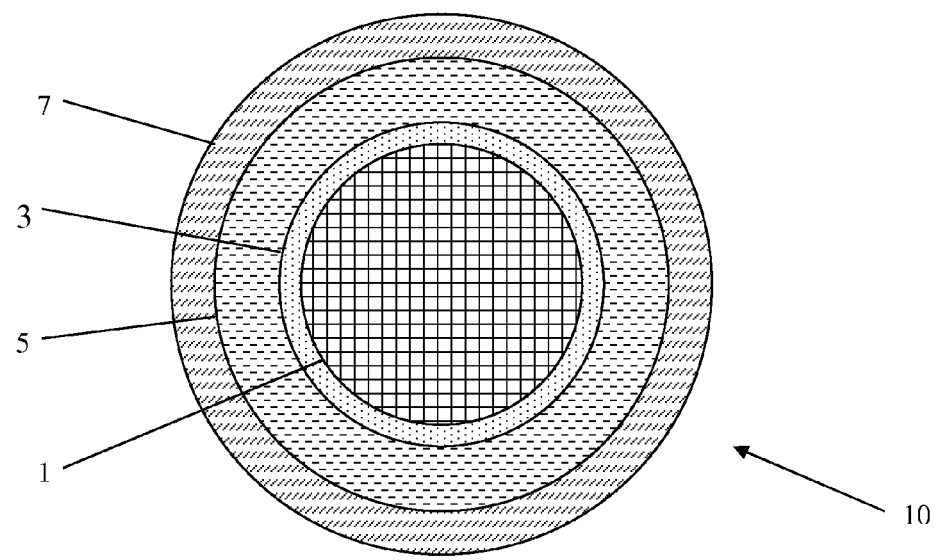
FIG. 1 shows a first exemplary embodiment of a controlled release bead.

Referring now to the drawings, in which like numerals refer to like components or steps, there are disclosed broad aspects of various exemplary embodiments.

FIG. 1 is a cross-sectional view of an exemplary embodiment of a controlled release bead 10 which allows for gradual release of the drug. The exemplary bead 10 includes an inert core 1 made of a water-soluble or water-swellable material. The core 1 may be made of a low molecular weight sugar, such as maltose, lactose, dextrose, or sucrose. Alternatively, the bead may be made of a hydrophilic polysaccharide, such as starch, microcrystalline cellulose, carboxymethylcellulose, croscarmellose, hydroxyethylcellulose, or hydroxypropyl methylcellulose. In various exemplary embodiments, the core 1 is made of a partially or completely water-soluble pharmaceutically acceptable inorganic salt. In various exemplary embodiments, the core 1 is made of a water-swellable synthetic polymer, such as crosslinked acrylic or methacrylic acid polymers and copolymers or crospovidone.

In various exemplary embodiments, coating 3 of a non-polymeric water-insoluble material is positioned on core 1. The non-polymeric water-insoluble material prevents water from entering into the core and causing the core to dissolve or swell. In various exemplary embodiments, the non-polymeric hydrophobic material is a fatty alcohol, a fatty carboxylic acid, a fatty carboxylic acid ester, a hydrogenated oil, a triglyceride fat, a wax, or a mixture thereof. In various exemplary embodiments, the non-polymeric hydrophobic material is a $C_{12}$-$C_{20}$ fatty alcohol, a $C_{12}$-$C_{20}$ fatty carboxylic acid, an ester of a $C_{12}$-$C_{20}$ fatty carboxylic acid, a hydrogenated vegetable oil, a triglyceride fat, or a mixture thereof. In various exemplary embodiments, the non-polymeric hydrophobic material is stearyl alcohol; cetyl alcohol; stearic acid; an ester of stearic acid with a lower alcohol or polyol, such as glyceryl monostearate; an ester of cetyl alcohol; hydrogenated castor oil; and a mixture thereof.

In various exemplary embodiments drug-containing coating 5 is positioned on non-polymeric water-insoluble material layer 3. Coating 5 may include a drug and, optionally, a binder. In various exemplary embodiments, the drug is a water-soluble drug. Suitable water-soluble drugs include tolterodine tartrate, diltiazem hydrochloride, verapamil hydrochloride, bupropion hydrochloride, metformin hydrochloride, propranolol hydrochloride, dextromethorphan hydrobromide, diphenhydramine hydrochloride, disopyramide hydrochloride, tramadol, fluoxetine hydrochloride, paroxetine hydrochloride, pentoxifylline hydrochloride and the like.

In various exemplary embodiments, the drug in coating 5 is an antimuscarinic, such as synthetic or semisynthetic muscarinic receptor antagonists. Such muscarinic receptor antagonists act on one or both of the M2 and M3 subtypes of muscarinic receptors. Suitable muscarinic receptor antagonists include dicyclomine, flavoxate, ipratropium, oxybutynin, pirenzepine, tiotropium, tolterodine, tropicamide, solifenacin, darifenacin, and combinations thereof.

In various exemplary embodiments, the drug in coating 5 is a synthetic or semisynthetic muscarinic receptor antagonists suitable for treating human or non-human mammalian patients with bladder control problems, such as urinary incontinence or enuresis. Suitable muscarinic receptor antagonists for treatment of patients with bladder control problems include oxybutynin, tolterodine, darifenacin, salts thereof, stereoisomers thereof, prodrugs thereof, and mixtures thereof.

In various exemplary embodiments, the drug in coating 5 is the (R)-enantiomer of tolterodine, the (R)-enantiomer of the 5-hydroxymethyl metabolite of tolterodine, the (S)-enantiomer of tolterodine, the 5-hydroxymethyl metabolite of the (S)-enantiomer of tolterodine, the racemate of tolterodine, a prodrug form of tolterodine, a pharmacologically acceptable salt of tolterodine, or a mixture thereof. The drug in coating 5 may be tolterodine L-tartrate.

In various exemplary embodiments, dosage forms containing a stabilized tolterodine L-tartrate composition as the drug in coating 5 are disclosed. Solid oral pharmaceutical compositions containing tolterodine tartrate as the active pharmaceutical ingredient (API) are found to be stabilized using at least one organic or mineral acid excipient. The use of one or more of these additives in a tablet or capsule pharmaceutical composition has been shown to decrease the formation of degradants and increase the stability of the composition.

Under certain conditions, such as those found in pharmaceutical tablets and capsules stored over time, tolterodine tartrate can undergo slow topochemical degradation, leading to a reduction in the potency and purity of the dosage form. The addition of at least one acidifying agent to tableted or encapsulated dosage forms of tolterodine tartrate can lead to a dramatic reduction of degradation, thereby providing improved quality and a longer useful shelf-life of the pharmaceutical dosage form. The inclusion of a pharmaceutically acceptable amount of a pH modifying compound into pharmaceutical compositions of tolterodine tartrate for the purpose of reducing the apparent pH of the composition improves the stability of the active pharmaceutical ingredient in the composition. In various exemplary embodiments, the pH modifying compound is an organic acid, a mineral acid, or a mixture thereof.

In various exemplary embodiments, the pH modifying compound within drug layer 5 would be one or more of the acidifying agents commonly used in the preparation of solid oral pharmaceutical compositions. These pH modifying compounds may be organic or mineral acids. In various exemplary embodiments, the pH modifying compounds are non-polymeric acids having at least a first $pK_a$ of less than 5.0, as shown in Table 1. In various exemplary embodiments, the pH modifying compounds may be acetic acid, benzoic acid, fumaric acid, lactic acid, malic acid, propionic acid, hydrochloric acid, phosphoric acid, sulfuric acid, stereoisomers thereof, or mixtures thereof. In various exemplary embodiments, the pH modifying compounds may be a solid acidifying agent selected from the group including tartaric acid, citric acid, ascorbic acid, stereoisomers thereof, or mixtures thereof. Pharmaceutically acceptable levels of these pH modifiers range from 0.1% to 10.0% of the pharmaceutical composition by weight. In various exemplary embodiments, the pH modifying acids are present in a range of from 0.4% to 2.5% by weight of the composition. In various exemplary embodiments, the pH modifying acids are present in a range of from 0.8% to 1.5% by weight.

TABLE 1

Exemplary pH Modifying Acids

| Acid | $pK_a$ |
| --- | --- |
| Acetic Acid | 4.76 |
| Benzoic Acid | 4.19 |
| Fumaric Acid | 3.03 |
| Lactic Acid | 4.14 |
| Malic Acid | 3.40 |
| Propionic Acid | 4.88 |
| Tartaric Acid | 2.93 |
| Citric Acid | 3.13 |
| Ascorbic Acid | 4.17 |
| Hydrochloric Acid | −8 |
| Sulfuric Acid | −3 |
| Phosphoric Acid | 2.15 |

In various exemplary embodiments, dosage forms containing stabilized tolterodine L-tartrate within drug layer 5 contain tolterodine L-tartrate stabilized with from 0.1 to 10 wt % of the dosage form of a pH modifying compound. In various exemplary embodiments, dosage forms contain tolterodine L-tartrate within drug layer 5, where tolterodine L-tartrate is stabilized with from 0.8 to 1.5 wt % of the dosage form of a pH modifying compound. In various exemplary embodiments, the pH modifying compound may be L-(+)-tartaric acid, D-(−)-tartaric acid, meso-tartaric acid, racemic tartaric acid, or a mixture thereof.

If desired, coating 5 may include a binder in addition to the drug. Suitable binders are typically water-soluble or water-swellable polymers. In various exemplary embodiments, water soluble binders include polyvinyl alcohol, polymers and copolymers of hydroxyalkyl acrylates and hydroxyalkyl methacrylates, polyvinylpyrrolidone, hydroxyethylcellulose, hydroxypropylcellulose, hydroxypropylmethylcellulose, polyethylene glycols, and combinations thereof. In various exemplary embodiments, water soluble binders include hydroxypropylmethylcellulose binders sold under the brand names Opadry II® Clear, Opadry® Clear, or a mixture thereof. Opadry II® Clear and Opadry® Clear, manufactured by Colorcon, Inc, USA, are used as an aqueous mixture containing hydroxypropylmethylcellulose.

A controlled release coating 7 is positioned on drug-containing layer 5. In various exemplary embodiments according to FIG. 1, the controlled release coating 7 is a layer of at least one pH-independent water-insoluble non-enteric polymer with or without a pore forming agent. The polymeric membrane in coating 7 becomes permeable upon exposure to aqueous environments within the human body, allowing the drug within underlying layer 5 to gradually leach through the release controlling coating 7. In various exemplary embodiments, the water-insoluble non-enteric polymer includes polyacrylic resins and cellulose derivatives such as cellulose ethers and cellulose esters. Suitable polymers include acrylic resins, preferably insoluble polymers or copolymers of alkyl acrylates or alkyl methacrylates, or water-insoluble celluloses such as ethylcellulose and cellulose acetate. In addition to the water-insoluble polymers, water-soluble polymers or non polymers may optionally be used in coating 7 in amounts of up to 50 wt. % as a pore forming agent to increase the permeability of the membrane and therefore increase the release rate of the active substance. In various exemplary embodiments, these pore forming agents are hydroxypropylmethylcellulose, hydroxyethyl cellulose, hydroxypropylcellulose, methylcellulose, carboxymethylcellulose, polyethylene glycol, polyvinylpyrrolidone, or polyvinyl alcohol. Opadry® Clear and Opadry II® Clear may be used as pore forming agents to increase the release rate of the active substance. Water-soluble non-polymeric pore-forming agents such as, for example, sucrose, lactose, mannitol, NaCl, and maltose may also be present in the release-controlling layer 7 of water-insoluble polymers to increase the release rate of the active substance.

In various exemplary embodiments, the release-controlling layer or membrane is comprised of at least one water-insoluble, non-pH dependent polymer with or without a pore forming agent. The release controlling membrane becomes permeable in an aqueous environment, thereby allowing release of the active ingredient. The pore former may be a water soluble or water mobile polymer or non polymer, organic or inorganic. In various exemplary embodiments, the release-controlling layer or membrane is comprised of two water-insoluble non-pH dependent polymers of different permeability with or without a pore forming agent. Alternatively, the release-controlling polymer is a pH dependent enteric polymer which is insoluble in the acidic gastric juices in the stomach (pH=1-3), but which is soluble in the more neutral environment of the small intestine (pH=6-8). In various exemplary embodiments, a composite release-controlling polymer membrane may include an inner layer of a water-insoluble, non-pH dependent polymer, and an outer layer of a pH dependent enteric polymer. In another exemplary embodiments, a composite release-controlling polymer membrane may include both water-insoluble, non-pH dependent polymer and pH dependent polymer with the later functioning as a pore forming agent.

If desired, the release rate of the active substance may be slowed in the acidic environment of the stomach by adding pH-sensitive enteric polymers to release controlling layer 7. These polymers do not dissolve until the bead enters the neutral environment of the small intestine. Suitable enteric polymers useful for this purpose include cellulose acetate phthalate, hydroxypropyl methylcellulose phthalate, cellulose acetate trimellitate, polymethacrylates, and an ammonium salt of a copolymer of methacrylic acid and methacrylic acid alkyl ester.

Figure 2:
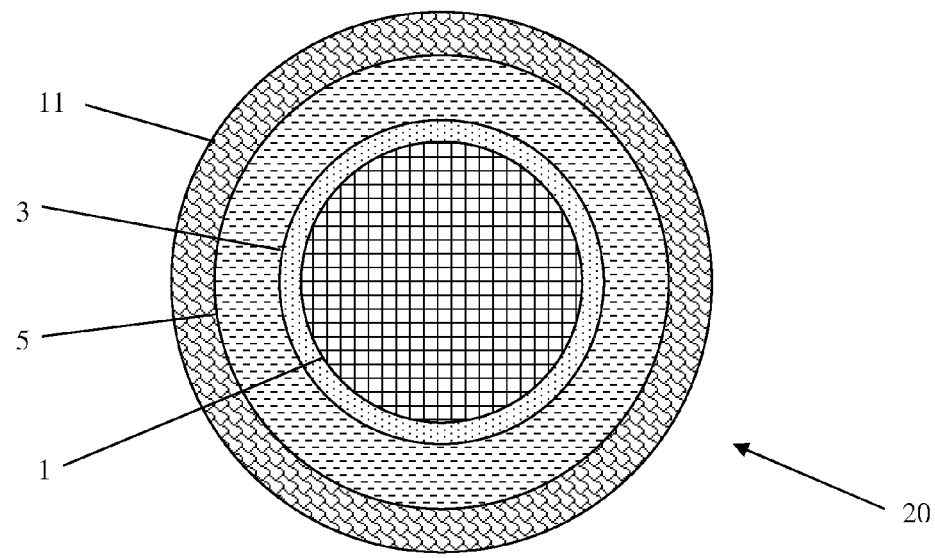
FIG. 2 shows a second exemplary embodiment of a controlled release bead.

FIG. 2 is a cross-sectional view of an exemplary embodiment of a controlled release bead 20 which prevents release of drug in the stomach. The exemplary bead 20 includes an inert core 1 made of a water-soluble or water-swellable material. A coating 3 of a non-polymeric water-insoluble material is positioned on core 1. A drug-containing coating 5 is positioned on non-polymeric water-insoluble material layer 3. A controlled release coating 11 is positioned on drug-containing layer 5. The constitution of core 1 and of coatings 3 and 5 is substantially identical to the constitution of core 1 and of coatings 3 and 5 in previously described bead 10, as shown in FIG. 1. However, controlled release coating 11, unlike the controlled release coating 7 on bead 10, is not a layer of a pH-independent water-insoluble non-enteric polymer. Rather, controlled release coating 11 on bead 20 is a layer of a pH-dependent enteric polymer. Accordingly, in the acidic environment of the stomach (pH 1-3), the pH-dependent enteric polymers in release controlling layer 11 are insoluble. These enteric polymers do not dissolve until the bead enters a neutral environment. Therefore, release controlling layer 11 remains intact in the stomach, but dissolves in the intestine (pH 6-8). This prevents the drug in layer 5 from being released until bead 20 enters the intestine. Once the bead is in the intestine, the dissolution of the release controlling layer rapidly releases the drug. Suitable enteric polymers useful for this purpose include cellulose acetate phthalate, hydroxypropyl methylcellulose phthalate, cellulose acetate trimellitate, polymethacrylates, and an ammonium salt of a copolymer of methacrylic acid and methacrylic acid alkyl ester.

Figure 3:
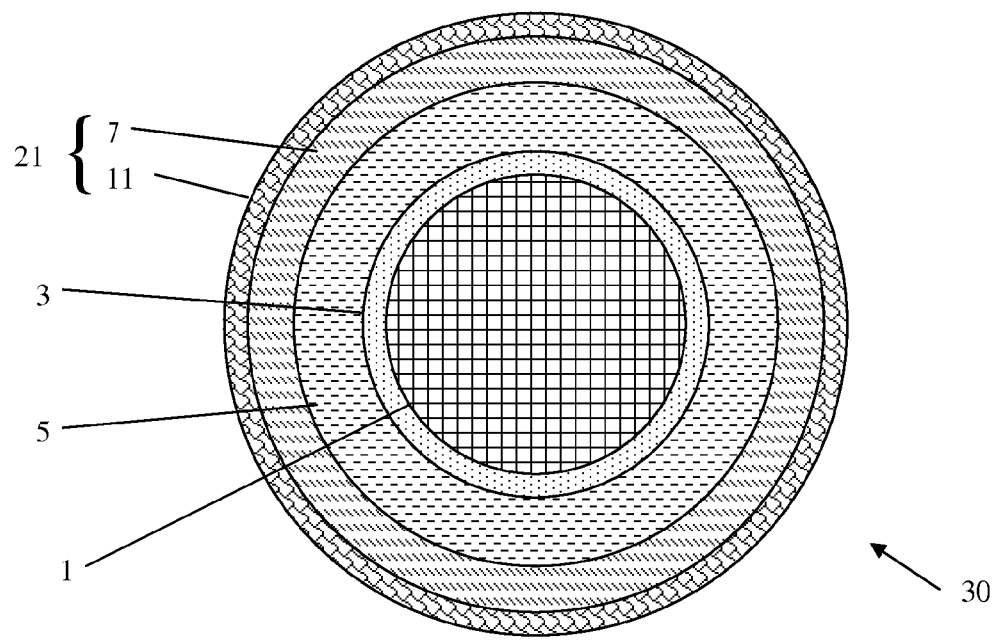
FIG. 3 shows a third exemplary embodiment of a controlled release bead.

FIG. 3 is a cross-sectional view of an exemplary embodiment of a controlled release bead 30 which both prevents release of drug in the stomach and allows for gradual release of the drug in the intestine. The exemplary bead 30 includes an inert core 1 made of a water-soluble or water-swellable material. A coating 3 of a non-polymeric water-insoluble material is positioned on core 1. A drug-containing coating 5 is positioned on non-polymeric water-insoluble material layer 3. A controlled release coating 21 is positioned on drug-containing layer 5. The constitution of core 1 and of coatings 3 and 5 is substantially identical to the constitution of core 1 and of coatings 3 and 5 in previously described beads 10 and 20, as shown in FIGS. 1 and 2. However, controlled release coating 21, unlike the controlled release coating 7 on bead 10 and the controlled release coating 11 on bead 20, is not a single layer of a controlled release polymer. Rather, coating 21 includes an inner controlled release layer 7 of a water-insoluble non-enteric polymer, and an outer layer 11 of a pH-dependent enteric polymer. The pH-dependent enteric polymers in outer layer 11 are insoluble in the acidic environment of the stomach (pH 1-3), thereby preventing any release of the drug in the stomach. These enteric polymers do not dissolve until the bead enters the neutral environment of the intestines (pH 6-8). After release controlling layer 11 dissolves in the intestine, the water-insoluble non-enteric polymer in layer 7 of bead 30 gradually erodes, allowing the drug in layer 5 to gradually escape from the bead by leaching through the inner release controlling layer 7.

In various exemplary embodiments, the enteric polymer in layer 11 of bead 30 may be cellulose acetate phthalate, hydroxypropyl methylcellulose phthalate, cellulose acetate trimellitate, polymethacrylates, or an ammonium salt of a copolymer of methacrylic acid and methacrylic acid alkyl ester. In various exemplary embodiments, the water-insoluble non-enteric polymer in layer 7 of bead 30 is selected from the group consisting of polyacrylic resins and cellulose derivatives selected from the group consisting of cellulose ethers and cellulose esters. Suitable polymers include acrylic resins, preferably insoluble polymers or copolymers of alkyl acrylates or alkyl methacrylates, or water-insoluble celluloses such as ethylcellulose and cellulose acetate. In addition to the water-insoluble non-enteric polymers, coating 7 of bead 30 may include water-soluble polymers in order to increase the release rate of the active substance in the intestine.

Figure 4:
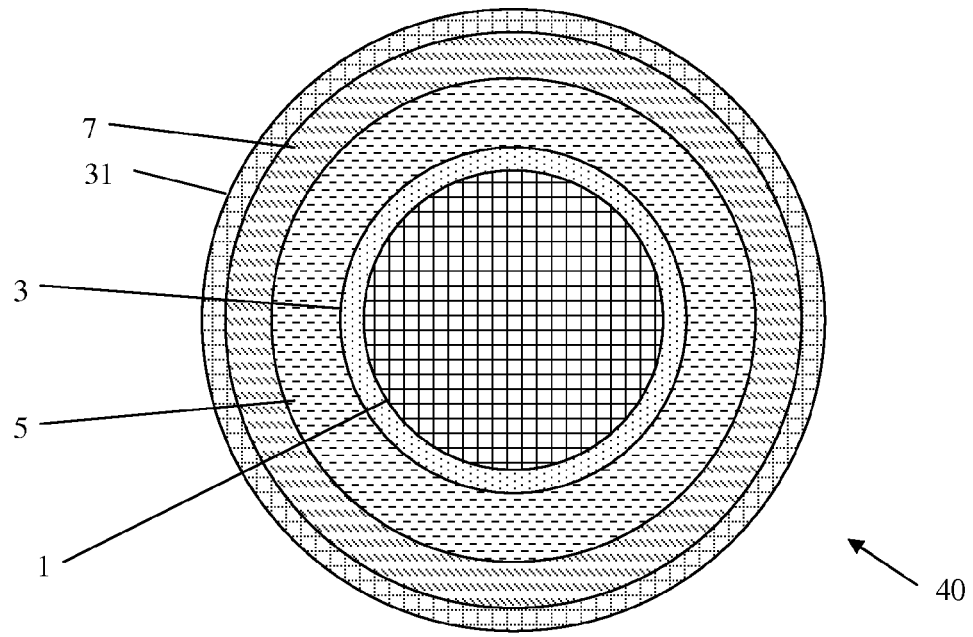
FIG. 4 shows a fourth exemplary embodiment of a controlled release bead.

FIG. 4 is a cross-sectional view of an exemplary embodiment of a controlled release bead 40 which allows for gradual release of a first drug in the intestine. The exemplary bead 40 includes an inert core 1 made of a water-soluble or water-swellable material. A coating 3 of a non-polymeric water-insoluble material is positioned on core 1. A drug-containing coating 5 is positioned on non-polymeric water-insoluble material layer 3. A controlled release coating 7 is positioned on drug-containing layer 5. The constitution of core 1 and of coatings 3, 5 and 7 is substantially identical to the constitution of core 1 and of coatings 3, 5 and 7 in previously described bead 10, as shown in FIG. 1. On top of controlled release coating 7 is deposited one or more additional layers 31 of water-soluble polymer. Such polymers may be a non-thermoplastic soluble polymer to decrease tackiness of the beads for subsequent processing, such as curing of the beads and/or filling the beads into capsules. Optionally, such an additional layer 31 of water soluble polymers may contain one or more second drugs for immediate release, where the second drugs may be the same as or different from the drug in the drug-containing layer 5. Suitable soluble polymers for layer 31 include hydroxypropyl methyl cellulose, hydroxyethyl cellulose, hydroxypropyl cellulose, methylcellulose, carboxymethylcellulose, polyethylene glycol, polyvinylpyrrolidone, and polyvinyl alcohol. Opadry® Clear or Opadry II® Clear may be used to form water soluble polymer coatings 31 in bead 40.

Figure 5:
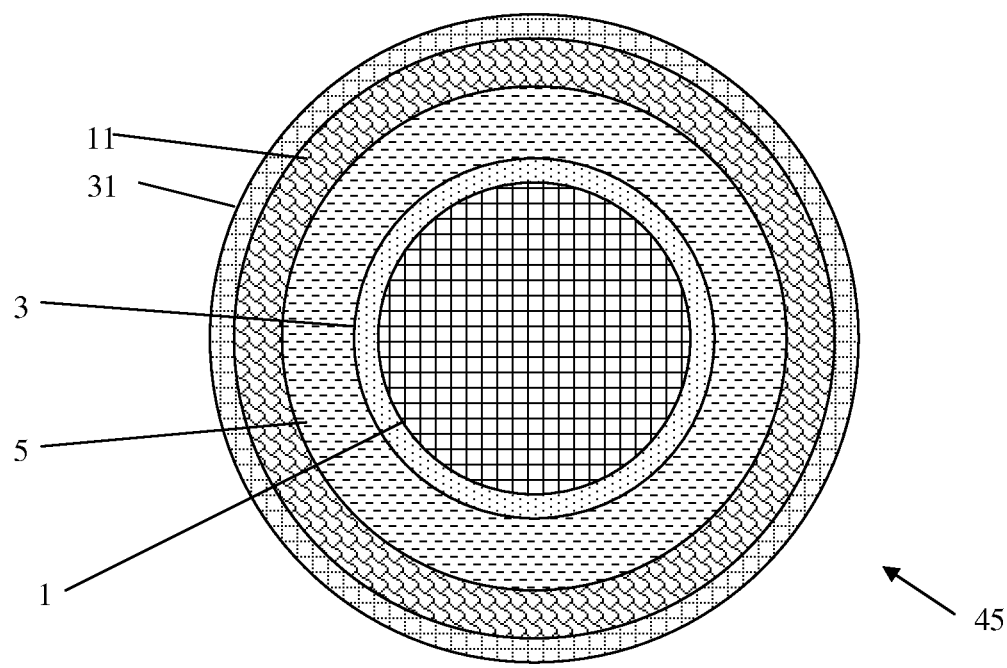
FIG. 5 shows a fifth exemplary embodiment of a controlled release bead.

FIG. 5 is a cross-sectional view of an exemplary embodiment of a controlled release bead 45 which allows for gradual release of a first drug in the intestine. In various exemplary embodiments, bead 45 may include an inert core 1; a coating of a non-polymeric water-insoluble material positioned on core 3; and a drug-containing coating positioned on layer 5. An enteric coating 11 may be positioned on drug-containing layer. On top of the enteric coating 11 is deposited one or more layers of water-soluble polymer 31, which may serve to reduce tackiness of the beads. Alternatively, the water-soluble polymer may contain an active ingredient for immediate release.

Figure 6:
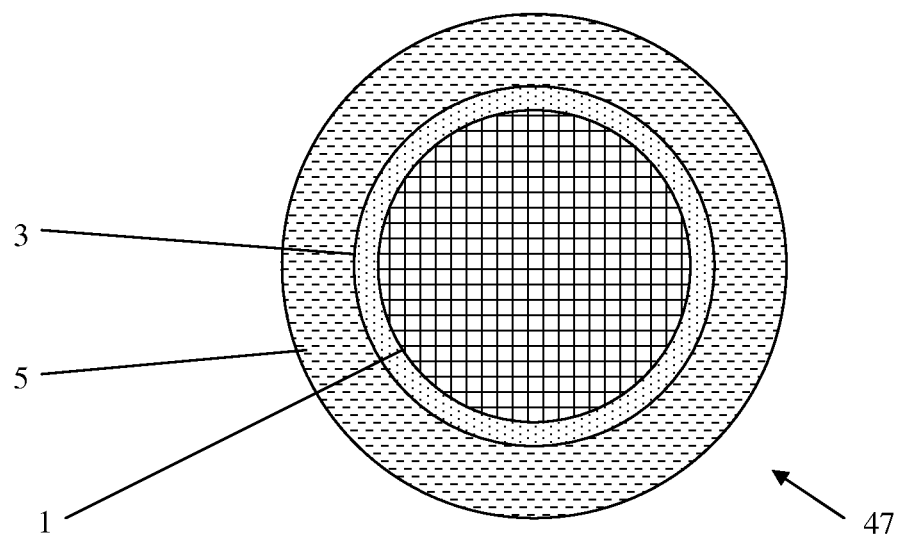
FIG. 6 shows a sixth exemplary embodiment of an immediate release bead.

FIG. 6 is a cross-sectional view of an exemplary embodiment of an immediate release bead 47. The exemplary bead 47 includes an inert core 1 made of a water-soluble or water-swellable material. A coating 3 of a non-polymeric water-insoluble material is positioned on core 1. A drug-containing coating 5 is positioned on non-polymeric water-insoluble material layer 3. The constitution of core 1 and of coatings 3 and 5 is substantially identical to the constitution of core 1 and of coatings 3 and 5 in previously described bead 10, as shown in FIG. 1. Since no controlled release polymer is present, the drug is released rapidly when exposed to an aqueous solution at physiological pH. If desired, an additional coating of a water-soluble or water-swellable polymer may be deposited on drug-containing coating 5. This additional coating may include polyvinyl alcohol, polymers and copolymers of hydroxyalkyl acrylates and hydroxyalkyl methacrylates, polyvinylpyrrolidone, hydroxyethylcellulose, hydroxypropyl methyl cellulose, polyethylene glycols, and combinations thereof.

In various exemplary embodiments, controlled release dosage forms comprising a plurality of beads are provided. Each of these beads includes an inert water-soluble or water-swellable core; a seal layer formed from a non-polymeric hydrophobic material positioned on said core layer; a layer containing at least one active ingredient positioned on said seal layer; and a layer of a release-controlling polymer positioned on said layer containing at least one active ingredient. In various exemplary embodiments, the beads may be beads 10, beads 20, beads 30, beads 40, beads 45, or mixtures thereof. In various exemplary embodiments, the controlled release dosage forms may be tablets. These controlled release tablets may be formed by compressing the plurality of beads in a mold. Prior to compression, the beads may be combined with various pharmaceutically acceptable tabletting excipients. Suitable tabletting excipients include binders such as croscarmellose sodium, crospovidone, gellan gum, hydroxypropyl cellulose, hydroxypropylmethylcellulose, povidone, sodium starch glycolate, and starch. Additional excipients may include calcium carbonate, dextrose, fructose, lactose, microcrystalline cellulose, maltodextrin, maltose, mannitol, microcrystalline cellulose, guar gum, sorbitol, and sucrose. In various exemplary embodiments, the controlled release tablets may be coated with an enteric coating subsequent to molding. In various exemplary embodiments, controlled release tablets coated with an enteric coating contain non-enteric coated beads; these non-enteric coated beads may be beads 10, beads 40, or mixtures thereof.

In various exemplary embodiments, the controlled release tablets contain at least one active ingredient in the controlled release beads, where the at least one active ingredient is a water-soluble drug. Suitable water-soluble drugs include tolterodine tartrate, diltiazem hydrochloride, verapamil hydrochloride, bupropion hydrochloride, metformin hydrochloride, propranolol hydrochloride, dextromethorphan hydrobromide, diphenhydramine hydrochloride, disopyramide hydrochloride, tramadol, fluoxetine hydrochloride, paroxetine hydrochloride, pentoxifylline hydrochloride and the like. In various exemplary embodiments, the drug in the controlled release beads is an antimuscarinic, such as synthetic or semisynthetic muscarinic receptor antagonists. Suitable muscarinic receptor antagonists include Dicyclomine, Flavoxate, Ipratropium, Oxybutynin, Pirenzepine, Tiotropium, Tolterodine, Tropicamide, Solifenacin, Darifenacin, and combinations thereof. In various exemplary embodiments, the drug in the controlled release beads is tolterodine tartrate.

In various exemplary embodiments, controlled release capsules containing a plurality of beads are provided. Each of these beads includes an inert water-soluble or water-swellable core; a seal layer formed from a non-polymeric hydrophobic material positioned on said core layer; a layer containing at least one active ingredient positioned on said seal layer; and a layer of a release-controlling polymer positioned on said layer containing at least one active ingredient. In various exemplary embodiments, the beads may be beads 10, beads 20, beads 30, beads 40, beads 45, or mixtures thereof. These controlled release capsules may be formed by filling a plurality of controlled release beads into a gelatin shell. In various exemplary embodiments, the controlled release capsules may be sealed with a polymeric coating subsequent to filling of beads into the shells; the polymeric coating may be made from a hydrophilic polymeric material, a hydrophilic polymeric material, or an enteric polymeric material. In various exemplary embodiments, controlled release capsules are coated with an enteric coating and contain non-enteric coated beads; these non-enteric coated beads may be beads 10, beads 40, or mixtures thereof.

In various exemplary embodiments, the controlled release capsules contain at least one active ingredient in the controlled release beads, where the at least one active ingredient is a water-soluble drug. Suitable water-soluble drugs include tolterodine tartrate, diltiazem hydrochloride, verapamil hydrochloride, bupropion hydrochloride, metformin hydrochloride, propranolol hydrochloride, dextromethorphan hydrobromide, diphenhydramine hydrochloride, disopyramide hydrochloride, tramadol, fluoxetine hydrochloride, paroxetine hydrochloride, pentoxifylline hydrochloride and the like. In various exemplary embodiments, the drug in the controlled release beads is an antimuscarinic, such as synthetic or semisynthetic muscarinic receptor antagonists. Suitable muscarinic receptor antagonists include Dicyclomine, Flavoxate, Ipratropium, Oxybutynin, Pirenzepine, Tiotropium, Tolterodine, Tropicamide, Solifenacin, Darifenacin, and combinations thereof. In various exemplary embodiments, the drug in the controlled release beads is tolterodine tartrate.

In various exemplary embodiments, the capsules or tablets containing the immediate release beads 47 or controlled release beads 10, beads 20, beads 30, beads 40, beads 45, or mixtures thereof may be used to treat a human or other mammal with enuresis, urinary incontinence, or other types of bladder control problems. This is done by administering one or more controlled release tablets or capsules containing an effective amount of an antimuscarinic agent approved for treatment of bladder control problems to the patient. Each controlled release tablet or capsule comprises a plurality of controlled release beads 10, controlled release beads 20, controlled release beads 30, controlled release beads 40, controlled release beads 45, or mixtures thereof. In various exemplary embodiments, each of the controlled release beads includes at least one antimuscarinic active ingredient selected from the group consisting of Oxybutynin, Tolterodine, Darifenacin, salts thereof, stereoisomers thereof, prodrugs thereof, metabolites thereof, and mixtures thereof. In various exemplary embodiments, the at least one active ingredient is selected from the group consisting of the (R)-enantiomer of tolterodine, the (R)-enantiomer of the 5-hydroxymethyl metabolite of tolterodine, the (S)-enantiomer of tolterodine, the 5-hydroxymethyl metabolite of the (S)-enantiomer of tolterodine, the racemate of tolterodine, prodrug forms of tolterodine, pharmacologically acceptable salts thereof, and mixtures thereof. In various exemplary embodiments, the at least one active ingredient is tolterodine tartrate.

Figure 7:
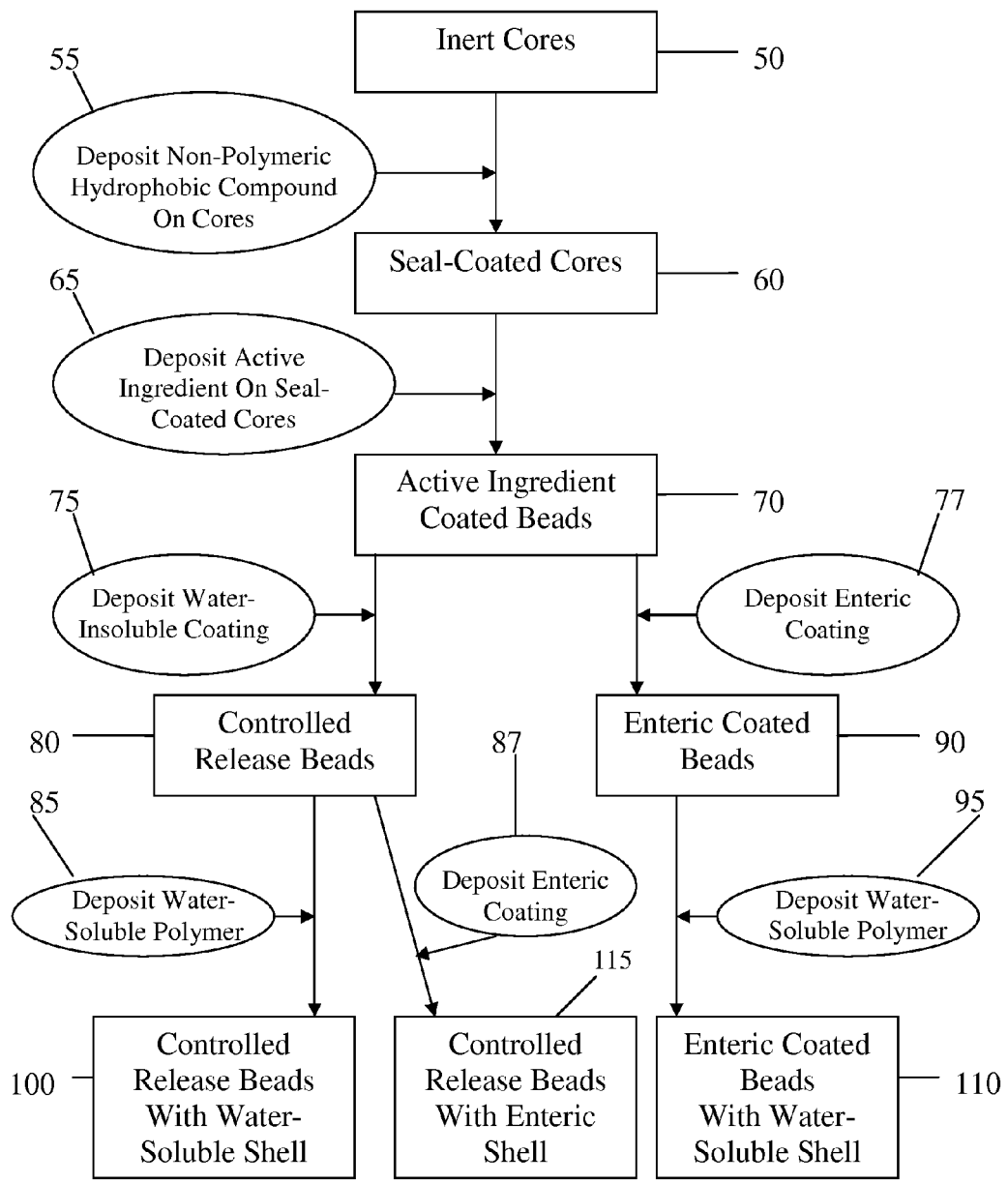
FIG. 7 shows a flow chart depicting the process by which various exemplary embodiments discussed herein are manufactured.

Various exemplary embodiments of methods of making a controlled release drug-containing bead will now be described with reference to the flow diagram of FIG. 7. The process begins with uncoated inert cores or beads 50. The cores 50 may be made of a hydrophilic polysaccharide, such as starch, microcrystalline cellulose, carboxymethylcellulose, croscarmellose, hydroxyethylcellulose, or hydroxypropyl methylcellulose. In various exemplary embodiments, the bead may be made of a partially or completely water-soluble pharmaceutically acceptable inorganic salt. In various exemplary embodiments, the bead may be made of a water-swellable synthetic polymer, such as crosslinked acrylic or methacrylic acid polymers and copolymers or crospovidone. In a first step 55, a seal layer is deposited on inert core 50 to produce seal-coated cores 60. The seal layer is formed from a non-polymeric hydrophobic material. In various exemplary embodiments, the non-polymeric hydrophobic material may be a fatty alcohol, a fatty carboxylic acid, a fatty carboxylic acid ester, a hydrogenated oil, a triglyceride fat, a wax, or a mixture thereof. In various exemplary embodiments, the non-polymeric hydrophobic material may be a $C_{12}$-$C_{20}$ fatty alcohol, a $C_{12}$-$C_{20}$ fatty carboxylic acid, an ester of a $C_{12}$-$C_{20}$ fatty carboxylic acid, a hydrogenated vegetable oil, a triglyceride fat, or a mixture thereof. In various exemplary embodiments, the non-polymeric hydrophobic material may be stearyl alcohol; cetyl alcohol; stearic acid; an ester of stearic acid with a lower alcohol or polyol, such as glyceryl monostearate; an ester of cetyl alcohol; hydrogenated castor oil; and a mixture thereof.

In various exemplary embodiments, step 55 of depositing a seal layer on said inert core 50 is performed by treating the inert core 50 with a non-aqueous solution or dispersion of the non-polymeric hydrophobic material. Suitable solvents for the non-aqueous solution or dispersion include ethanol, isopropyl alcohol, acetone, and lower alkanes or cycloalkanes. In various exemplary embodiments, step 55 of depositing a seal layer on said inert core 50 is performed by treating the inert core 50 with an aqueous solution or dispersion of the non-polymeric hydrophobic material. In various exemplary embodiments, step 55 of depositing a seal layer on said inert core 50 is performed by treating inert core 50 with a low-melting non-polymeric hydrophobic material in a molten state. This may be done by spraying the non-polymeric hydrophobic molten material onto core 50, or dipping core 50 into a pool of molten non-polymeric hydrophobic material.

Referring again to FIG. 7, in a second step 65, a layer containing an active ingredient is deposited on seal-coated core 60 to produce active ingredient-coated beads 70. In various exemplary embodiments, the layer deposited in step 65 includes a drug and, optionally, a binder. In various exemplary embodiments, the drug is a water-soluble drug. Suitable water-soluble drugs include tolterodine tartrate, diltiazem hydrochloride, verapamil hydrochloride, bupropion hydrochloride, metformin hydrochloride, propranolol hydrochloride, dextromethorphan hydrobromide, diphenhydramine hydrochloride, disopyramide hydrochloride, tramadol, fluoxetine hydrochloride, paroxetine hydrochloride, pentoxifylline hydrochloride and the like. In various exemplary embodiments, the drug deposited in step 65 is an antimuscarinic. Suitable muscarinic receptor antagonists include dicyclomine, flavoxate, ipratropium, oxybutynin, pirenzepine, tiotropium, tolterodine, tropicamide, solifenacin, darifenacin, and combinations thereof.

In various exemplary embodiments, the drug deposited in step 65 is a synthetic or semisynthetic muscarinic receptor antagonists suitable for treating human or non-human mammalian patients with bladder control problems, such as urinary incontinence or enuresis. Suitable muscarinic receptor antagonists for treatment of patients with bladder control problems include oxybutynin, tolterodine, darifenacin, salts thereof, stereoisomers thereof, prodrugs thereof, and mixtures thereof. In various exemplary embodiments, the drug in coating 5 is the (R)-enantiomer of tolterodine, the (R)-enantiomer of the 5-hydroxymethyl metabolite of tolterodine, the (S)-enantiomer of tolterodine, the 5-hydroxymethyl metabolite of the (S)-enantiomer of tolterodine, the racemate of tolterodine, a prodrug form of tolterodine, a pharmacologically acceptable salt of tolterodine, or a mixture thereof. The drug deposited in step 65 may be tolterodine L-tartrate. In various exemplary embodiments, the drug deposited in step 65 is acid-stabilized tolterodine L-tartrate, where the acid-stabilized tolterodine L-tartrate is prepared by mixing tolterodine L-tartrate with a stabilizing amount of a non-polymeric pH modifying acid having a $pK_a$ of less than 5.0. The tolterodine L-tartrate may be mixed with the acid prior to deposition or during deposition.

If desired, the binder deposited in step 65 in addition to the drug may be a water-soluble polymer. In various exemplary embodiments, water soluble binders include polyvinyl alcohol, polymers and copolymers of hydroxyalkyl acrylates and hydroxyalkyl methacrylates, polyvinylpyrrolidone, hydroxyethylcellulose, hydroxypropylmethylcellulose, polyethylene glycols, and combinations thereof.

In various exemplary embodiments, step 65 of depositing a layer containing at least one active ingredient is performed by coating the seal-coated cores 60 with a non-aqueous solution or dispersion of said at least one active ingredient and, optionally, a binder; or coating the seal-coated cores 60 with an aqueous solution or dispersion of said at least one active ingredient and, optionally, a binder.

In various exemplary embodiments, beads 70 may be used as immediate-release drug-containing beads. Alternatively, active ingredient-coated beads 70 containing a water-soluble binder in the layer containing the active ingredient may be segregated into two groups. If desired, a first group of beads 70 may be set aside and reserved for use as immediate release drug containing beads, where the active ingredient is released upon dissolution of the water-soluble binder. A second group of beads 70 is coated with a controlled release polymer. These portions may then be recombined and used to produce dosage forms having a first portion of drug which undergoes immediate release, and a second portion of drug which undergoes controlled release.

Referring again to FIG. 7, the process of making controlled release beads 80 having non-enteric coatings from active ingredient-coated beads 70 will now be described. In a third step 75, a layer of a non-enteric release-controlling polymer is deposited on active-ingredient-coated beads 70 to produce controlled release beads 80. Step 75 of depositing a layer of a non-enteric release-controlling polymer is performed by coating said layer containing at least one active ingredient with a non-aqueous solution or dispersion of said release-controlling polymer; or coating said seal layer with an aqueous solution or dispersion of said release-controlling polymer. Controlled release beads 80 may be used in preparation of controlled release tablets or capsules, as previously described. If desired, controlled release beads 80 may be combined with active ingredient-coated beads 70, which have been held in reserve for use as immediate release beads, prior to preparation of tablets or capsules. This allows preparation of a dosage form which allows immediate release of one portion of the drug, and release of a second portion of the drug over an extended period of time.

In various exemplary embodiments, the non-enteric release-controlling polymer deposited in step 75 is a water-insoluble non-enteric polymer selected from the group consisting of polyacrylic resins and cellulose derivatives selected from the group consisting of cellulose ethers and cellulose esters. Suitable polymers include acrylic resins, preferably insoluble polymers or copolymers of alkyl acrylates or alkyl methacrylates, or water-insoluble celluloses such as ethylcellulose and cellulose acetate. In step 75, water-soluble polymers may be combined with the water-insoluble non-enteric polymer in amounts of up to 30 wt. %. These soluble polymers may be hydroxypropylmethyl cellulose, hydroxyethyl cellulose, hydroxypropyl cellulose, methylcellulose, carboxymethylcellulose, polyethylene glycol, polyvinylpyrrolidone, or polyvinyl alcohol.

Referring again to FIG. 7, the process of making controlled release beads 90 having enteric coatings from ingredient-coated beads 70 will now be described. In a third step 77, a layer of an enteric polymer is deposited on active-ingredient-coated beads 70 to produce enteric coated beads 90. Suitable enteric polymers useful for this purpose include cellulose acetate phthalate, hydroxypropyl methylcellulose phthalate, cellulose acetate trimellitate, polymethacrylates, and an ammonium salt of a copolymer of methacrylic acid and methacrylic acid alkyl ester. Step 77 of depositing a layer of an enteric polymer on the layer containing the active ingredient is performed by coating the layer containing the active ingredient with a non-aqueous solution or dispersion of the enteric polymer; coating the layer containing the active ingredient with an aqueous dispersion of enteric polymer; or coating the layer containing the active ingredient with a solution of the enteric polymer in aqueous acid, and then treating the enteric coated beads with aqueous base to neutralize the enteric polymer. Enteric coated beads 90 may be used in preparation of controlled release tablets or capsules, as previously described. If desired, enteric coated beads 90 may be combined with active ingredient-coated beads 70, which have been held in reserve for use as immediate release beads, prior to preparation of tablets or capsules. This allows preparation of a dosage form which allows immediate release of one portion of the drug, and subsequent release of a second portion of the drug, after the beads pass from the stomach into the intestine.

Referring again to FIG. 7, an alternate method of making controlled release beads having enteric coatings from ingredient-coated beads 70 will now be described. This method produces controlled release beads having enteric shells. In a step 75, a layer of a non-enteric release-controlling polymer is deposited on active-ingredient-coated beads 70 to produce controlled release beads 80, as previously described. Next, in step 87, a layer of an enteric polymer is deposited on controlled release beads 80 to produce enteric coated beads 115. Deposition of the enteric polymer in step 87 is carried out in essentially the same manner as deposition of the enteric polymer in step 77. The resulting beads have enteric coatings on top of water-insoluble controlled release coatings. The enteric coatings do not dissolve in the stomach, but remain intact until the bead enters the neutral environment of the intestine (pH 6-8). After the enteric coatings dissolve in the intestine, the water-insoluble non-enteric polymer layer beneath gradually erodes, allowing the drug in the bead to gradually escape by leaching through the water-insoluble non-enteric polymer layer. Enteric coated beads 115 may be used in preparation of controlled release tablets or capsules, as previously described.

Referring again to FIG. 7, a method of making controlled release beads having water-soluble polymeric coatings will now be described. This method produces controlled release beads having soluble shells. In step 85, a layer of a water-soluble polymer is deposited on controlled release beads 80 to produce controlled release beads having water soluble shells 100. Similarly, in step 95, a layer of a water-soluble polymer is deposited on enteric coated beads 90 to produce enteric coated beads with water-soluble shells 110. Deposition of the water-soluble polymer in step 95 is carried out in essentially the same manner as deposition of the water-soluble polymer in step 85. The polymers in the soluble shells may be used as binders for immediate release drug containing layers, or for polymers used to reduce tackiness of the finished beads. The layer of water soluble polymer may contain immediate release drugs, which may be the same as or different from the drug in the drug-containing layer deposited in step 65. Suitable soluble polymers for the layer of water soluble polymer include hydroxypropylmethylcellulose, hydroxyethyl cellulose, hydroxypropyl cellulose, methylcellulose, carboxymethylcellulose, polyethylene glycol, polyvinylpyrrolidone, and polyvinyl alcohol. Beads 110 and 110 may be used in preparation of controlled release tablets or capsules, as previously described.

Additional exemplary embodiments of pharmaceutical dosage forms contain stabilized tolterodine L-tartrate. These exemplary embodiments are solid oral dosage forms comprising an effective amount of tolterodine L-tartrate and pharmaceutically acceptable excipients, wherein the tolterodine L-tartrate is stabilized with a pharmaceutically acceptable non-polymeric pH-modifying acid having a $pK_a$ of less than 5.0. The acid may be hydrochloric acid, phosphoric acid, sulfuric acid, acetic acid, benzoic acid, fumaric acid, lactic acid, malic acid, propionic acid, tartaric acid, citric acid, ascorbic acid, stereoisomers thereof, or mixtures thereof.

In various exemplary embodiments, solid oral dosage forms containing stabilized tolterodine L-tartrate are controlled release dosage forms. These controlled release dosage form comprise acid-stabilized tolterodine L-tartrate and a release-controlling polymer. In various exemplary embodiments, the acid-stabilized tolterodine L-tartrate is dispersed in the release-controlling polymer, where the release-controlling polymer is a pH-insensitive water-insoluble polymer. The drug is released by erosion of the polymer upon exposure to an aqueous environment under physiological conditions. The polymer may be a polymer or copolymer of alkyl acrylates or alkyl methacrylates, a cellulose ether such as ethylcellulose, or a cellulose ester.

In various exemplary embodiments, the acid-stabilized tolterodine L-tartrate present in a core layer of the dosage form. The drug-containing core layer is coated by a layer of a release-controlling polymer, where the release-controlling polymer is a pH-insensitive water-insoluble polymer or an enteric polymer. In dosage forms where the release-controlling polymeric coating is a pH-insensitive water-insoluble polymer, the drug is released by erosion of the polymer upon exposure to an aqueous environment under physiological conditions. The pH-insensitive water-insoluble polymer may be a polymer or copolymer of alkyl acrylates or alkyl methacrylates, a cellulose ether such as ethylcellulose, or a cellulose ester. The enteric polymer may be cellulose acetate phthalate, hydroxypropyl methylcellulose phthalate, cellulose acetate trimellitate, polymethacrylates, or an ammonium salt of a copolymer of methacrylic acid and methacrylic acid alkyl ester. In dosage forms where the release-controlling polymeric coating is an enteric polymer, the drug is released upon dissolution of the enteric coating in the intestines.

In various exemplary embodiments, solid oral dosage forms containing stabilized tolterodine L-tartrate are immediate release dosage forms. These immediate release dosage forms contain acid-stabilized tolterodine L-tartrate and a water-swellable or water-soluble polymer. In various exemplary embodiments, the acid-stabilized tolterodine L-tartrate is dispersed in said water-swellable or water-soluble polymeric binder. Non-limiting examples of water-swellable or water-soluble polymers which may be used in such exemplary embodiments include hydroxypropylmethyl cellulose, hydroxyethyl cellulose, hydroxypropyl cellulose, methylcellulose, carboxymethylcellulose, polyethylene glycol, polyvinylpyrrolidone, and polyvinyl alcohol. Hydroxypropylmethyl cellulose is a useful water-swellable or water-soluble polymer which may be used in a commercially available form, such as Opadry® Clear or Opadry II® Clear. The acid-stabilized tolterodine L-tartrate and the water-swellable or water-soluble polymeric binder may be provided as a homogeneous composition. This composition may be prepared by mixing the tolterodine L-tartrate with a stabilizing amount of an acid, such as tartaric acid; mixing the resulting acid-stabilized tolterodine L-tartrate with a water-swellable or water-soluble polymeric binder; and compressing the mixture to form tablets or filling the mixture into a capsule shell. The total amount of tolterodine L-tartrate in the final dosage form may range 0.5 to 4 mg.

In various exemplary embodiments, the immediate release solid oral dosage form may be a non-homogeneous dosage form including a core layer containing the acid-stabilized tolterodine L-tartrate and a layer containing a water-swellable or water-soluble polymer polymer. The layer containing the acid-stabilized tolterodine L-tartrate is surrounded by the layer of said water-swellable or water-soluble polymer polymer. The layer containing the acid-stabilized tolterodine L-tartrate contains, in addition to the drug, disintegrants such as microcrystalline cellulose, carboxymethylcellulose, sodium starch glycolate, or mixtures thereof. The outer layer of a water-swellable or water-soluble polymer contains hydroxypropylmethylcellulose, hydroxyethylcellulose, hydroxypropylcellulose, methylcellulose, carboxymethylcellulose, polyethylene glycol, polyvinylpyrrolidone, polyvinyl alcohol, or a mixture thereof. The layer containing the acid-stabilized tolterodine L-tartrate may be a core layer of said dosage form, and the layer containing said water-swellable or water-soluble polymer surrounds the core layer. This composition may be prepared by mixing the tolterodine L-tartrate with a stabilizing amount of an acid, such as tartaric acid; mixing the resulting acid-stabilized tolterodine L-tartrate with a disintegrant; and compressing the resulting mixture to form tolterodine L-tartrate containing cores. The cores are then coated with a water-swellable or water-soluble polymeric binder.

In various exemplary embodiments, the solid oral dosage form may be a non-homogeneous dosage form including an inert core, a layer containing the acid-stabilized tolterodine L-tartrate surrounding the core, and a layer containing a water-swellable or water-soluble polymer. The layer containing said water-swellable or water-soluble polymer surrounds the acid-stabilized tolterodine L-tartrate layer. This composition may be prepared by mixing the tolterodine L-tartrate with a stabilizing amount of an acid, such as tartaric acid, and coating the inert cores with the resulting acid-stabilized tolterodine L-tartrate. The drug-coated cores may be coated with a water-swellable or water-soluble polymeric binder to produce an immediate release dosage form, or with a controlled release polymer to produce a controlled release dosage form.

In various exemplary embodiments, a seal layer may be deposited on the inert cores prior to coating the inert cores with the acid-stabilized tolterodine L-tartrate. The seal layer, if used in the acid-stabilized tolterodine L-tartrate dosage form, may be prepared from a hydrophilic polymer, a hydrophobic polymer, or a water-insoluble non-polymeric material. The water-insoluble non-polymeric material is selected from the group consisting of a fatty alcohol, a fatty carboxylic acid, a fatty carboxylic acid ester, a hydrogenated oil, a triglyceride fat, a wax, and mixtures thereof. In various exemplary embodiments, the non-polymeric hydrophobic material in the seal layer is selected from the group consisting of stearyl alcohol, cetyl alcohol, stearic acid, an ester of stearic acid with a lower alcohol or polyol, an ester of cetyl alcohol, hydrogenated castor oil, and mixtures thereof.

In various exemplary embodiments, tablets containing acid stabilized tolterodine-L-tartrate may be prepared. The method of preparing tablets includes a first step of mixing tolterodine-L-tartrate with a pharmaceutically acceptable pH-modifying acid to obtain an acid-stabilized tolterodine-L-tartrate. The acid-stabilized tolterodine-L-tartrate is then combined with at least one pharmaceutically acceptable excipient to form an acid-stabilized mixture. The pharmaceutically acceptable excipients usable with acid-stabilized tolterodine-L-tartrate include microcrystalline cellulose, sucrose, hydroxypropylmethylcellulose, sodium starch glycolate, starch, xylitol, fructose, sorbitol, calcium phosphate, calcium sulfate, magnesium stearate, oleic acid, stearic acid, stearyl alcohol, calcium carbonate, dextrose, lactose, polyvinylpyrrolidone, crosslinked polyvinylpyrrolidone, silica, titanium dioxide, gelatin, triglycerides, or a mixture thereof. The acid-stabilized mixture is then compressed to form a tablet. In a further step, the tablet may be coated with a polymer. The polymer may be a hydrophilic polymer, such as hydroxypropylmethylcellulose, or a hydrophobic controlled release polymer, such as ethylcellulose.

In various exemplary embodiments, capsules containing acid stabilized tolterodine-L-tartrate may be prepared. The method of preparing capsules includes a first step of mixing tolterodine-L-tartrate with a pharmaceutically acceptable pH-modifying acid to obtain an acid-stabilized tolterodine-L-tartrate. The acid-stabilized tolterodine-L-tartrate is then combined with at least one pharmaceutically acceptable excipient to form an acid-stabilized mixture. The pharmaceutically acceptable excipients usable with acid-stabilized tolterodine-L-tartrate include microcrystalline cellulose, sucrose, hydroxypropylmethylcellulose, sodium starch glycolate, starch, xylitol, fructose, sorbitol, calcium phosphate, calcium sulfate, magnesium stearate, oleic acid, stearic acid, stearyl alcohol, calcium carbonate, dextrose, lactose, polyvinylpyrrolidone, crosslinked polyvinylpyrrolidone, silica, titanium dioxide, gelatin, triglycerides, or a mixture thereof. The acid-stabilized mixture is then filled into a capsule shell. In a further step, the capsule may be coated with a polymer. The polymer may be a hydrophilic polymer, such as hydroxypropylmethylcellulose, or a hydrophobic controlled release polymer, such as ethylcellulose.

The invention will now be described in more detail by the following non-limiting Examples.

EXAMPLE 1

An exemplary capsule containing 4 mg/unit acid-stabilized tolterodine L-tartrate as active ingredient comprises a plurality of beads. Each bead includes as an inert core, a sugar sphere, 20-25 mesh (20/25). As a first seal layer, stearyl alcohol is deposited on the sugar sphere. Next, a layer containing Tolterodine L-tartrate, tartaric acid, and an Opadry II Clear dispersion containing hydroxypropylmethylcellulose (HPMC) is deposited on the seal layer. Finally, a third layer of Surelease® and Opadry Clear is deposited on the Tolterodine L-tartrate layer as a release-controlling layer. The ratio of Surelease® solids:Opadry Clear is 80:20. Surelease® is an aqueous film-coating dispersion, about 25% solids, and is manufactured by Colorcon, Inc, USA.

Beads with a three-layer coating having the above characteristics were prepared as follows:

2900 g of sugar spheres, 20-25 mesh, were charged into a rotor fluid bed coater and sprayed with a solution of 725 g of stearyl alcohol dissolved in isopropyl alcohol to produce stearyl alcohol coated beads. In the same rotor, 983.6 g of the stearyl alcohol coated beads were sprayed with a solution of 26 g Tolterodine L-tartrate, 8.21 g tartaric acid, and 8.55 g Opadry® Clear (Opadry® Clear, manufactured by Colorcon Inc, USA, includes hydroxypropylmethylcellulose) in a mixed solvent containing water and isopropyl alcohol in a 4:1 ratio. The beads are then coated with a sustained release coating liquid of an ethylcellulose aqueous suspension composed of Surelease® and Opadry® Clear in a ratio of 80:20 w/w solids.

After drying, the coated spheres were filled into gelatin capsules to obtain 4 mg tolterodine L-tartrate capsules. Each capsule contained 180 mg beads, giving capsules of the composition shown in Table 2; the final composition contained 0.8 wt. % tartaric acid.

TABLE 2

Formulation of Tolterodine Tartrate Capsules

| Component | mg/unit |
|---|---|
| Sugar Spheres 20/25 | 121.06 |
| Stearyl Alcohol | 30.26 |
| Tolterodine L-tartrate | 4.00 |
| Tartaric Acid | 1.26 |
| Opadry II ® Clear | 1.32 |
| Surelease Ethylcellulose Suspension | 17.68 |
| Opadry ® Clear | 4.42 |
| Total | 180.0 |

In an analogous manner to the procedure described in Example 1 above, other exemplary bead formulations containing tolterodine L-tartrate as the active ingredient were prepared as described in Examples 2, 3, and 4 below.

EXAMPLE 2

Tolterodine L-tartrate capsules were prepared by the process described in Example 1, except for the step of coating the beads with a sustained release coating liquid of an ethylcellulose aqueous suspension composed of Surelease® and Opadry® Clear. In this Example, the ethylcellulose aqueous suspension was composed of Surelease® and Opadry® Clear in a ratio of 85:15 w/w solids.

EXAMPLE 3

Tolterodine L-tartrate capsules were prepared by the process described in Example 1, except for the step of coating the beads with a sustained release coating liquid of an ethylcellulose aqueous suspension composed of Surelease® and Opadry® Clear. In this Example, the ethylcellulose aqueous suspension was composed of Surelease® and Opadry® Clear in a ratio of 75:25 w/w solids.

EXAMPLE 4

Tolterodine L-tartrate capsules were prepared by the process described in Example 1, except for the step of coating the beads with a sustained release coating liquid of an ethylcellulose aqueous suspension composed of Surelease® and Opadry® Clear. In this Example, the ethylcellulose aqueous suspension was composed of Surelease® and Opadry® Clear in a ratio of 82.5:17.5 w/w solids.

EXAMPLE 5

A study of the effect of the composition of the controlled release layer was performed. The effect of the controlled release layer on drug release was tested as follows. Four lots of Tolterodine L-tartrate capsules according to Examples 1 through 4. In the first lot, prepared according to Example 1, the ratio of Surelease® solids:Opadry Clear solids in the controlled release layer is 80:20. In the second lot, prepared according to Example 2, the ratio of Surelease® solids:Opadry Clear solids in the controlled release layer is 85:15. In the third lot, prepared according to Example 3, the ratio of Surelease® solids:Opadry Clear solids in the controlled release layer is 75:25. In the fourth lot, prepared according to Example 4, the ratio of Surelease® solids:Opadry Clear solids in the controlled release layer is 82.5:17.5.

Figure 8:
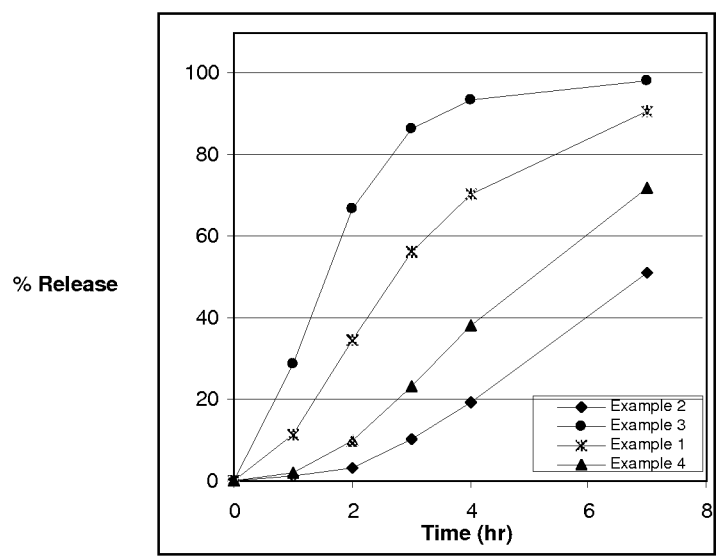
FIG. 8 shows dissolution of active ingredient from tolterodine tartrate capsules containing various exemplary embodiments of the controlled release beads discussed herein.

The in vitro drug release rate was measured at 37° C. in a phosphate buffer of pH 6.8. The USP dissolution test apparatus I was used at 100 rpm. The results are shown in the diagrams in FIG. 8. As shown in FIG. 8, as the percentage of plasticized ethylcellulose (Surelease®) in the controlled release layer increases, the drug release rate decreases. For the capsules of Example 3, where Surelease® makes up 75% of the controlled release layer, essentially 100% of the Tolterodine L-tartrate was released after 7 hr. For the capsules of Example 2, where Surelease® makes up 85% of the controlled release layer, only 50% of the Tolterodine L-tartrate was released after 7 hr. Additionally, the capsules of Example 2 exhibit nearly linear, zero order release of Tolterodine L-tartrate over a range of time beginning approximately 2 hr after the start of the test to at least a time of 7 hr after the start of the test. Further, it is seen that the capsules of Example 4, where Surelease® makes up 82.5% of the controlled release layer, also exhibit nearly linear, zero order release of Tolterodine L-tartrate over a range of time of 1 hr after the start of the test to at least a time of 7 hr after the start of the test.

EXAMPLE 6

An exemplary capsule containing 4 mg/unit tolterodine L-tartrate as active ingredient comprises a plurality of beads; no organic stabilizing acid was included in the drug layer. Each bead includes as an inert core, a sugar sphere, 20-25 mesh (20/25). As a first seal layer, stearyl alcohol is deposited on the sugar sphere. Next, a layer of Tolterodine L-tartrate and hydroxypropylmethylcellulose (HPMC) is deposited on the seal layer. Finally, a third layer of Surelease® and HPMC is deposited on the Tolterodine L-tartrate layer as a release-controlling layer. Surelease® is an aqueous film-coating dispersion, about 25% solids, and is manufactured by Colorcon, Inc, USA.

Beads with a three-layer coating having the above characteristics were prepared as follows:

Sugar spheres, 20-25 mesh, were charged into a rotor fluid bed coater and sprayed with a solution of stearyl alcohol dissolved in isopropyl alcohol (20 wt. % stearl alcohol) to produce stearyl alcohol coated beads. In the same rotor, stearyl alcohol coated beads were coated with Tolterodine L-tartrate and Opadry® Clear. This is done by spray coating in three stages, with an initial coating of aqueous Opadry® Clear; a second coating of a solution of 26 g Tolterodine L-tartrate and Opadry® Clear; and a third coating of Opadry® Clear. The resulting Tolterodine L-tartrate/Opadry® Clear coating contains Tolterodine L-tartrate and Opadry® Clear solids in a 4:1 ratio. The beads are then coated with a sustained release coating liquid of an ethylcellulose aqueous suspension composed of Surelease® and Opadry® Clear in a ratio of 85:15 w/w solids.

After drying, the coated spheres were filled into gelatin capsules to obtain 4 mg tolterodine L-tartrate capsules. Each capsule contained 180 mg beads, giving capsules of the composition shown in Table 3.

TABLE 3

Formulation of Tolterodine Tartrate Capsules

| Component | mg/unit |
|---|---|
| Sugar Spheres 20/25 | 120.83 |
| Stearyl Alcohol | 24.17 |
| Tolterodine L-tartrate | 4.00 |
| Tartaric Acid | 0.00 |
| Opadry ® Clear (in drug layer) | 1.00 |
| Surelease Ethylcellulose Suspension | 25.50 |
| Opadry ® Clear (in sustained release coating) | 4.50 |
| Total | 180.0 |

EXAMPLE 7

A study of the effect of a stabilizing amount of tartaric acid on the degradation of the tolterodine L-tartrate was performed. The effect of the tartaric acid was tested by exposing capsules prepared according to Example 6, with no acid stabilizer, and capsules of Example 1, containing 0.8 wt. % tartaric acid stabilizer, to elevated temperate and humidity (40° C. and 75% relative humidity). Concentrations of total degradation products, an unknown degradation product, and tolterodine monomer degradant were monitored over time. Tolterodine dimer and tolterodine tartrate 4B are other known degradation products; however, since concentrations of these products were essentially constant over the course of stability experiments, they were not individually reported. As a comparison, formation of degradation products in the commercially available tolterodine tartrate extended release formulation Detrol® LA was also monitored.

As seen in Table 4, Detrol® LA has an initial impurity level of 0.37 wt. %. After three months of exposure to elevated temperate and humidity, the impurity level has increased to 1.27 wt. %. The formulation of Example 6, which has no acid stabilizer, and the formulation of Example 1, which has 0.8 wt. % acid stabilizer, each exhibit very low initial concentrations of impurities. In each case, the initial impurity level is 0.05 wt. %. After three months of exposure to elevated temperate and humidity, Example 6 has a significantly increased level of impurities, with an impurity level of 1.17 wt. %. Acid-stabilized Example 1, on the other hand, has a much lower level of impurities, with an impurity level of 0.16 wt. %.

TABLE 4

Tolterodine Capsule Formulations - Accelerated Stability

| Lot | Stability Timepoint | Monomer Degradant (%) | Unknown Degradant (%) | Total Impurity Level (%) |
|---|---|---|---|---|
| Detrol ® LA | Initial | 0.05 | 0.25 | 0.37 |
| Commercially available | 1 month | 0.12 | 0.50 | 0.70 |
| formulation | 2 month | 0.26 | 0.96 | 1.29 |
|  | 3 month | 0.26 | 0.93 | 1.27 |
| Example 6 | Initial | 0.05 | LT 0.07 | 0.05 |
| Bead formulation | 1 month | 0.19 | 0.55 | 0.74 |
| without acid stabilizer | 3 month | 0.28 | 0.89 | 1.17 |
| Example 1 | Initial | 0.05 | LT 0.05 | 0.05 |
| Bead formulation with | 1 month | LT 0.05 | LT 0.05 | LT 0.05 |
| 0.8 wt % tartaric acid | 2 month | 0.05 | LT 0.05 | 0.05 |
|  | 3 month | 0.05 | 0.11 | 0.16 |

EXAMPLE 8

An exemplary capsule containing 4 mg/unit tolterodine L-tartrate as active ingredient comprises a plurality of beads.

Each bead includes as an inert core, a sugar sphere, 20-25 mesh (20/25). As a first seal layer, stearic acid is deposited on the sugar sphere. Next, a layer of Tolterodine L-tartrate and hydroxypropylmethylcellulose (HPMC) is deposited on the seal layer. Finally, a third layer of Surelease® and HPMC is deposited on the Tolterodine L-tartrate layer as a release-controlling layer. The ratio of Surelease® solids:HPMC is 75:25.

Beads with a three-layer coating having the above characteristics were prepared as follows:

1047.3 g of sugar spheres, 20-25 mesh, were charged into a rotor fluid bed coater and sprayed with a solution of 104.7 g of stearic acid dissolved in isopropyl alcohol/water (9:1) to produce stearic acid coated beads. In the same rotor, 1045 g of the stearic acid coated beads were sprayed with a solution of 29.03 g Tolterodine L-tartrate and 14.51 g Opadry® Clear in a mixed solvent containing water and isopropyl alcohol in a 4:1 ratio. The HPMC is obtained as Opadry® Clear. The beads are then coated with a sustained release coating liquid of an ethylcellulose aqueous suspension composed of Surelease® and Opadry® Clear in a ratio of 75:25 w/w solids.

After drying, the coated spheres were filled into gelatin capsules to obtain 4 mg tolterodine L-tartrate capsules. Each capsule contained 180 mg beads, giving capsules of the composition shown in Table 5.

TABLE 5

Formulation of Tolterodine Tartrate Capsules

| Component | mg/unit |
| --- | --- |
| Sugar Spheres 20/25 | 130.91 |
| Stearic Acid | 13.09 |
| Tolterodine L-tartrate | 4.00 |
| Opadry ® Clear in drug layer | 2.00 |
| Surelease Ethylcellulose Suspension | 22.50 |
| Opadry ® Clear in sustained release coating | 7.50 |
| Total | 180.0 |

Although various exemplary embodiments have been described in detail with particular reference to certain exemplary aspects thereof, it should be understood that the subject matter disclosed herein is capable of other different embodiments, and its details are capable of modifications in various obvious respects. As is readily apparent to those skilled in the art, variations and modifications can be affected while remaining within the spirit and scope of the disclosure. Accordingly, the foregoing disclosure, description, and figures are for illustrative purposes only, and do not in any way limit the invention, which is defined only by the claims.

What is claimed is:

1. A method of making a drug-containing bead, said method comprising the steps of:
   combining tolterodine-L-tartrate with a stabilizing amount of a pharmaceutically acceptable non-polymeric pH-modifying acid having a $pK_a$ of less than 5.0 to obtain an acid-stabilized tolterodine-L-tartrate composition which does not contain oxybutynin;
   depositing a seal layer on an inert core, said seal layer being formed from a non-polymeric hydrophobic material; and
   depositing a layer containing said acid-stabilized tolterodine-L-tartrate on said seal layer.

2. The method of claim 1, wherein the pH-modifying acid is a non-polymeric acid having at least a first $pK_a$ of less than 5.0.

3. The method of claim 1, wherein the pH-modifying acid is selected from the group consisting of acetic acid, benzoic acid, fumaric acid, lactic acid, malic acid, propionic acid, hydrochloric acid, phosphoric acid, sulfuric acid, tartaric acid, citric acid, ascorbic acid, stereoisomers thereof, and mixtures thereof.

4. The method of claim 1, wherein said layer containing said acid-stabilized tolterodine-L-tartrate is an immediate release layer.

5. The method of claim 4, wherein said immediate release layer further comprises a water-soluble or water-swellable polymer.

6. The method of claim 1, further comprising a step of depositing a layer containing a controlled-release polymer on said layer containing said acid-stabilized tolterodine-L-tartrate.

7. A method of making a solid pharmaceutical composition, said method comprising the steps of:
   combining tolterodine-L-tartrate in solid form with a stabilizing amount of a pharmaceutically acceptable non-polymeric pH-modifying acid having a $pK_a$ of less than 5.0 to obtain a solid acid-stabilized tolterodine-L-tartrate composition which does not contain oxybutynin; and
   combining said solid acid-stabilized tolterodine-L-tartrate composition with at least one pharmaceutically acceptable excipient to form a solid acid-stabilized mixture.

8. The method of claim 7, wherein the pH-modifying acid is selected from the group consisting of acetic acid, benzoic acid, fumaric acid, lactic acid, malic acid, propionic acid, hydrochloric acid, phosphoric acid, sulfuric acid, tartaric acid, citric acid, ascorbic acid, stereoisomers thereof, and mixtures thereof.

9. The method of claim 7, wherein said pharmaceutical composition is a tablet;
   said method further comprising the step of compressing said acid-stabilized mixture to form said tablet.

10. The method of claim 9, wherein said at least one pharmaceutically acceptable excipient comprises microcrystalline cellulose, hydroxypropylmethylcellulose, sodium starch glycolate, starch, xylitol, fructose, sorbitol, calcium phosphate, calcium sulfate, calcium carbonate, dextrose, lactose, polyvinylpyrrolidone, crosslinked polyvinylpyrrolidone, or a mixture thereof.

11. The method of claim 9, further comprising a step of coating said tablet with a polymer.

12. The method of claim 11, wherein said polymer is hydroxypropylmethylcellulose.

13. The method of claim 11, wherein said polymer is ethylcellulose.

14. The method of claim 7, wherein said pharmaceutical composition is a capsule;
   said method further comprising the step of filling said acid-stabilized mixture into a capsule shell.

15. The method of claim 14, wherein said at least one pharmaceutically acceptable excipient comprises microcrystalline cellulose, hydroxypropylmethylcellulose, sodium starch glycolate, starch, xylitol, fructose, sorbitol, calcium phosphate, calcium sulfate, calcium carbonate, dextrose, lactose, polyvinylpyrrolidone, crosslinked polyvinylpyrrolidone, or a mixture thereof.

16. The method of claim 15, further comprising a step of coating said capsule with a polymer.

17. The method of claim 16, wherein said polymer is hydroxypropylmethylcellulose.

18. The method of claim 16, wherein said polymer is ethylcellulose.

19. The method of claim 7, wherein said pharmaceutical composition is a drug-containing bead;
   said method further comprising the steps of:
   depositing a seal layer on an inert core, said seal layer being formed from a non-polymeric hydrophobic material; and
   depositing a layer containing said acid-stabilized mixture on said seal layer.

20. The method of claim 19, wherein said at least one pharmaceutically acceptable excipient is a water-swellable or water-soluble polymeric binder.

* * * * *